US007807143B2

(12) United States Patent
Brod (10) Patent No.: US 7,807,143 B2
(45) Date of Patent: Oct. 5, 2010

(54) ALPHA-MSH THERAPIES FOR TREATMENT OF AUTOIMMUNE DISEASE

(75) Inventor: Staley A. Brod, Bellaire, TX (US)

(73) Assignee: Research Development Foundation, Carson City, NV (US)

( * ) Notice: Subject to any disclaimer, the term of this patent is extended or adjusted under 35 U.S.C. 154(b) by 156 days.

(21) Appl. No.: 11/874,058

(22) Filed: Oct. 17, 2007

(65) Prior Publication Data

US 2009/0060868 A1 Mar. 5, 2009

Related U.S. Application Data

(60) Provisional application No. 60/829,915, filed on Oct. 18, 2006.

(51) Int. Cl.
*A61K 38/19* (2006.01)
*A61K 45/00* (2006.01)
(52) U.S. Cl. ........................ 424/85.4; 514/12
(58) Field of Classification Search ................ None
See application file for complete search history.

(56) References Cited

U.S. PATENT DOCUMENTS

| 2,904,471 | A | 9/1959 | Kuehl, Jr. .................... 514/12 |
| 2,992,165 | A | 7/1961 | Thompson ................... 514/12 |
| 4,554,101 | A | 11/1985 | Hopp ........................ 530/324 |
| 4,874,744 | A | 10/1989 | Nordlund et al. .............. 514/13 |
| 5,028,592 | A | 7/1991 | Lipton ........................ 514/18 |
| 5,157,023 | A | 10/1992 | Lipton ........................ 514/18 |
| 5,359,030 | A | 10/1994 | Ekwuribe .................... 530/303 |
| 5,674,839 | A | 10/1997 | Hruby et al. .................... 514/9 |
| 5,714,576 | A | 2/1998 | Hruby et al. ................ 530/312 |
| 6,338,834 | B1 | 1/2002 | Jurisson et al. ............ 424/1.69 |
| 7,169,603 | B2 | 1/2007 | Hedley et al. ............ 435/320.1 |
| 2002/0193332 | A1 | 12/2002 | Hedley ........................ 514/44 |
| 2005/0239170 | A1 | 10/2005 | Hedley et al. .............. 435/69.4 |
| 2007/0185030 | A1 | 8/2007 | Brod ........................... 514/13 |

FOREIGN PATENT DOCUMENTS

| DE | 3345358 | 6/1985 |
| DE | 3731875 | 3/1989 |
| EP | 0146113 | * 6/1985 |
| WO | WO 02/06316 | 1/2002 |
| WO | WO 2005/072271 | 8/2005 |
| WO | WO 2005/123107 | 12/2005 |
| WO | WO 2006/021814 | 3/2006 |

OTHER PUBLICATIONS

PCT International Preliminary Report on Patentability, issued in International Application No. PCT/US2007/081656, mailed Apr. 30, 2009.
Sandman et al., "An analog of MSH/ACTH 4-9 enhances interpersonal and environmental awareness in mentally retarded adults," *Peptides*, 1:109-114, 1980.
International Search Report and Written Opinion issued in International Application No. PCT/US2007/081656, dated May 19, 2008.
Brod et al., "Ingested (oral) alpha-MSH inhibits acute EAE," *Cytokine*, 39(1):4, 2007.
Brod et al., "Ingested (oral) alpha-MSH inhibits acute EAE," *Journal of Neuroimmunology*, 193:106-112, 2008.
Rajora et al., "Alpha-MSH modulates experimetnal inflammatory bowel disease," *Peptides*, 18(3):381-385, 1997.
Yin et al., "Generation of expression constructs that secrete bioactive alpha-MSH and their use ni the treatment of experimetnal autoimmune encephalomyelitis," *Gene Therapy*, 10(4):348-355, 2003.
U.S. Appl. No. 08/844,731, filed Apr. 21, 1997, Brod.
Bergh et al., "Monthly intravenous methylprednisolone in relapsing-remitting multiple sclerosis—Reduction of enhancing lesions, T2 lesion volume and plasma prolactin concentrations," *BMC Neurology*, 6:19, 2006.
Brod and Burns, "Suppression of relapsing experimental autoimmune encephalomyelitis in the SJL/J mouse by oral administration of type I interferons," *Neurology*. 44:1144-1148, 1994.
Brod et al., "Oral administration of human or murine interferon alpha suppresses relapses and modifies adoptive transfer in experimental autoimmune encephalomyelitis," *J Neuroimmunol*. 58:61-69, 1995.
Filippini et al., "Corticosteroids or ACTH for acute exacerbations in multiple sclerosis," *Cochrane Database Syst. Rev.*, 4:CD001331, 2000.
Hoggard et al., "Peripherally administered [Nle$^4$,$_D$-Phe$^7$]-alpha-melanocyte stimulating hormone increases resting metabolic rate, while peripheral agouti-related protein has no effect, in wild type C57BL/6 and ob/ob mice," *J. Mol. Endocrinology*, 33:693-703, 2004.
Luger et al., "New insights into the functions of alpha-MSH and related peptides in the immune system," *Ann N Y Acad Sci.*, 994:133-140, 2003.
Mahmood et al., "Selection of the first-time dose in humans: comparison of different approaches based on interspecies scaling of clearance," *J. Clin. Pharmacol.*, 43:692-697, 2003.
McDonold et al., "Recommended diagnostic criteria for multiple sclerosis: guidelines from the International Panel on the diagnosis of multiple sclerosis," *Ann. Neurol.*, 50:121-127, 2001.
Miranda and Alewood, "Accelerated chemical synthesis of peptides and small proteins," *Proc. Natl. Acad. Sci. USA*, 96:1181-1186, 1999.
Moustafa et al., "Inhibition of tumor necrosis factor-alpha stimulated NFkappaB/p65 in human keratinocytes by alpha-melanocyte stimulating hormone and adrenocorticotropic hormone peptides," *J. Invest. Dermatol.*, 119:1244-1253, 2002.
Namba et al., "Induction of regulatory T cells by the immunomodulating cytokines alpha-melanocyte-stimulating hormone and transforming growth factor-beta2," *J Leukoc Biol.*, 72:946-952, 2002.
Peters, "The Self-Similarity of the Melanocortin System," *Endocrinology*, 146:529-531, 2005.

(Continued)

Primary Examiner—Bridget E Bunner
Assistant Examiner—Fozia M Hamud
(74) Attorney, Agent, or Firm—Fulbright & Jaworski LLP (57) ABSTRACT

Methods and compositions for the enteral treatment of autoimmune disease such a multiple sclerosis with polypeptide therapeutics. Enteral therapeutics comprise monomeric alpha-MSH polypeptides such as ACTH. Therapeutic formulations of the invention may be used to reduce the incidence or severity of autoimmune disease. For instance methods for the oral treatment of multiple sclerosis with alpha-MSH and ACTH are described.

10 Claims, 4 Drawing Sheets

OTHER PUBLICATIONS

Scholzen et al., "alpha-Melanocyte Stimulating Hormone Prevents Lipopolysaccharide-Induced Vasculitis by Down-Regulating Endothelial Cell Adhesion Molecule Expression," *Endocrinology*, 144:360-370, 2003.

Taylor and Namba, "In vitro induction of CD25+ CD4+ regulatory T cells by the neuropeptide alpha-melanocyte stimulating hormone (alpha-MSH)," *Immunol Cell Biol.*, 79:358-367, 2001.

Taylor et al., "Neuropeptide regulation of immunity. The immunosuppressive activity of alpha-melanocyte-stimulating hormone (alpha-MSH)," *Ann N Y Acad Sci.*, 917:239-247, 2000.

Taylor, "Modulation of Regulatory T Cell Immunity by the Neuropeptide Alpha-Melanocyte Stimulating Hormone," *Cell Mol Biol (Noisy-le-grand)*, 49:143-149, 2003.

Van der Zee et al., "alpha-MSH and Org.2766 in peripheral nerve regeneration: different routes of delivery," *Eur. J. Pharmacol.*, 147:351-357, 1988.

* cited by examiner

SEQUENCE LISTING

<160> NUMBER OF SEQ ID NOS: 13

<210> SEQ ID NO 1
<211> LENGTH: 21
<212> TYPE: PRT
<213> ORGANISM: Mus musculus

<400> SEQUENCE: 1

Met Glu Val Gly Trp Tyr Arg Ser Pro Phe Ser Arg Val Val His Leu
1               5                   10                  15

Tyr Arg Asn Gly Lys
            20

<210> SEQ ID NO 2
<211> LENGTH: 13
<212> TYPE: PRT
<213> ORGANISM: Homo sapiens

<400> SEQUENCE: 2

Ser Tyr Ser Met Glu His Phe Arg Trp Gly Lys Pro Val
1               5                   10

<210> SEQ ID NO 3
<211> LENGTH: 39
<212> TYPE: PRT
<213> ORGANISM: Sus scrofa domestica

<400> SEQUENCE: 3

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Gln Leu Ala
            20                  25                  30

Glu Ala Phe Pro Leu Glu Phe
        35

<210> SEQ ID NO 4
<211> LENGTH: 39
<212> TYPE: PRT
<213> ORGANISM: Sus scrofa

<400> SEQUENCE: 4

```
Ser Tyr Ser Met Glu His Phe Arg Trp Gly Lys Pro Val Gly Lys Lys
1               5                   10                  15
Arg Arg Pro Val Lys Val Tyr Pro Asn Gly Ala Glu Asp Glu Leu Ala
            20                  25                  30
Glu Ala Phe Pro Leu Glu Phe
        35
```

<210> SEQ ID NO 5
<211> LENGTH: 39
<212> TYPE: PRT
<213> ORGANISM: Homo sapiens

<400> SEQUENCE: 5

```
Ser Tyr Ser Met Glu His Phe Arg Trp Gly Lys Pro Val Gly Lys Lys
1               5                   10                  15
Arg Arg Pro Val Lys Val Tyr Pro Asn Gly Ala Glu Asp Glu Ser Ala
            20                  25                  30
Glu Ala Phe Pro Leu Glu Phe
        35
```

<210> SEQ ID NO 6
<211> LENGTH: 39
<212> TYPE: PRT
<213> ORGANISM: Homo sapiens

<400> SEQUENCE: 6

```
Ser Tyr Ser Met Glu His Phe Arg Trp Gly Lys Pro Val Gly Lys Lys
1               5                   10                  15
Arg Arg Pro Val Lys Val Tyr Pro Asn Gly Ala Asp Asp Glu Ser Ala
            20                  25                  30
Glu Ala Phe Pro Leu Glu Phe
        35
```

<210> SEQ ID NO 7
<211> LENGTH: 39
<212> TYPE: PRT
<213> ORGANISM: Bos taurus

<400> SEQUENCE: 7

```
Ser Tyr Ser Met Glu His Phe Arg Trp Gly Lys Pro Val Gly Lys Lys
1               5                   10                  15
Arg Arg Pro Val Lys Val Tyr Pro Asn Gly Ala Glu Asp Glu Ser Ala
            20                  25                  30
Gln Ala Phe Pro Leu Glu Phe
        35
```

<210> SEQ ID NO 8
<211> LENGTH: 39
<212> TYPE: PRT
<213> ORGANISM: Canis familiaris

<400> SEQUENCE: 8

```
Ser Tyr Ser Met Glu His Phe Arg Trp Gly Lys Pro Val Gly Lys Lys
1               5                   10                  15
Arg Arg Pro Val Lys Val Tyr Pro Asn Gly Ala Glu Asp Glu Ser Ala
```

```
                    20                  25                  30

Glu Ala Phe Pro Val Glu Phe
        35

<210> SEQ ID NO 9
<211> LENGTH: 39
<212> TYPE: PRT
<213> ORGANISM: Loxodonta africana

<400> SEQUENCE: 9

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Gly Glu Ser Ala
            20                  25                  30

Glu Ala Phe Pro Leu Glu Phe
        35

<210> SEQ ID NO 10
<211> LENGTH: 39
<212> TYPE: PRT
<213> ORGANISM: Saguinus oedipus

<400> SEQUENCE: 10

Ser Tyr Ser Met Glu His Phe Arg Trp Gly Lys Pro Val Gly Lys Lys
1               5                   10                  15

Arg Arg Pro Val Lys Val Tyr Pro Asn Ser Ala Glu Asn Glu Ser Ala
            20                  25                  30

Glu Ala Phe Pro Leu Glu Phe
        35

<210> SEQ ID NO 11
<211> LENGTH: 39
<212> TYPE: PRT
<213> ORGANISM: Cavia porcellus

<400> SEQUENCE: 11

Ser Tyr Ser Met Glu His Phe Arg Trp Gly Lys Pro Val Gly Lys Lys
1               5                   10                  15

Arg Arg Pro Val Lys Val Tyr Ala Asn Gly Ala Glu Glu Glu Ser Ala
            20                  25                  30

Glu Ala Phe Pro Leu Glu Phe
        35

<210> SEQ ID NO 12
<211> LENGTH: 39
<212> TYPE: PRT
<213> ORGANISM: Rattus norvegicus

<400> SEQUENCE: 12

Ser Tyr Ser Met Glu His Phe Arg Trp Gly Lys Pro Val Gly Lys Lys
1               5                   10                  15

Arg Arg Pro Val Lys Val Tyr Pro Asn Val Ala Glu Asn Glu Ser Ala
            20                  25                  30

Glu Ala Phe Pro Leu Glu Phe
        35

<210> SEQ ID NO 13
<211> LENGTH: 39
<212> TYPE: PRT
<213> ORGANISM: Artificial
<220> FEATURE:
```

```
<223> OTHER INFORMATION: General ACTH Sequence
<220> FEATURE:
<221> NAME/KEY: misc_feature
<222> LOCATION: (24)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 13

Ser Tyr Ser Met Glu His Phe Arg Trp Gly Lys Pro Val Gly Lys Lys
1               5                   10                  15

Arg Arg Pro Val Lys Val Tyr Xaa Xaa Xaa Ala Xaa Xaa Xaa Xaa Ala
            20                  25                  30

Xaa Ala Phe Pro Xaa Glu Phe
            35
```

ALPHA-MSH THERAPIES FOR TREATMENT OF AUTOIMMUNE DISEASE

This application claims the benefit of priority to U.S. Provisional Patent Application No. 60/829,915, filed Oct. 18, 2006, the entire contents of which are specifically incorporated herein.

BACKGROUND OF THE INVENTION

1. Field of the Invention

The invention generally concerns the field of immunology, and more specifically concerns the treatment of autoimmune and inflammatory disease. Proteinaceous compositions described herein may be used as enteral therapeutics for the treatment or prevention of autoimmune and inflammatory disorders.

2. Description of Related Art

Autoimmune and disease result when an immune system of a subject mounts a response against the subject's own cells or proteins. In part because of the chronic nature of these diseases, effective treatment has proved difficult. One model system that is widely used in the study of autoimmune disease is the experimental autoimmune encephalomyelitis (EAE) model. EAE is a T cell mediated inflammatory autoimmune process of the central nervous system (CNS) that resembles the human demyelinating disease multiple sclerosis (MS) (Alvord et al., 1965). This model provides a useful animal system for the evaluation of potential therapies for human autoimmune and disease (Raine et al., 1977; Wisnewski & Keith 1977; Feuer et al., 1985). Previous studies using the EAE model have demonstrated that immunoactive proteins such as type I interferon administered orally (ingested) can inhibit clinical attacks in acute rat EAE and suppresses clinical relapse and inflammation in murine chronic relapsing EAE (U.S. patent application Ser. No. 08/844,731; Brod & Burns 1994; Brod et al., 1995).

Alpha-melanocyte stimulating hormone (MSH) is a short amino acid hormone that is processed in vivo from the hormonal precursor proteins proopiomelanocortin (POMC) and adrenocorticotropic hormone (ACTH). The purification and activation of alpha-MSH precursors, such as ACTH has been previously described in U.S. Pat. Nos. 2,904,471 and 2,992,165. Furthermore, synthetic analogs of alpha-MSH have been developed as therapeutics and imaging agents for use in a variety of diseases (U.S. Pat. No. 6,338,834). However, it is not clear whether such analogs maintain the full repertoire of therapeutic functionality possessed by intact alpha-MSH polypeptides.

Alpha-MSH itself immono-modulates inflammation via melanocortin receptor (MC-1R)-expressing monocytes, macrophages, and dendritic cells (DCs) (Luger et al., 2003) and via primed regulatory (MC5r)-expressing antigen-specific CD25$^+$CD4$^+$ Treg cells (Tayor et al., 2001; Taylor 2003). Interestingly, alpha-MSH generated autoantigen-specific Treg cells can adoptively transfer protection against autoimmunity (Namba et al, 2002), significantly impair TNF-α-induced lymphocyte adhesion and cell adhesion molecules (CAMs) E-selectin, VCAM-1, and ICAM-1 (Scholzen et al., 2003) and DTH (Taylor et al., 2000). Crude ACTH formulations such as those described in PCT Appln. WO2006/021814 may be used to treat a variety of autoimmune diseases and cancers. Also, U.S. Pat. No. 4,874,744 concerns alpha-MSH formulations for treating dermatitis. More recently, U.S. Pat. No. 7,169,603 described alpha-MSH concatamers and their use in treating a variety of disease states. Nonetheless, methods for effective treatment of autoimmune diseases by enteral administration of alpha-MSH have not previously been described. In fact, previous studies seemed to indicate that alpha-MSH may not be active when administered orally (Van der Zee et al., 1988).

SUMMARY OF THE INVENTION

In a first embodiment, there is provided a method for treating or delaying the onset of an autoimmune disease in a subject comprising administering to the subject an effective dose of an alpha-MSH monomer. Methods according to invention will generally involve contacting an alpha-MSH monomer with epithelial cells of a subject. For example, an alpha-MSH monomer may be administered intraocularly (e.g., via eye drops), enterically, intravaginally, intranasally or topically. As used herein enteric administration means administration through the digestive tract. Thus, enteric administration comprises oral and anal administration. In preferred embodiment, an alpha-MSH monomer is administered to a subject orally.

As used herein an alpha-MSH monomer means a polypeptide molecule comprising a single iteration of an alpha-MSH amino acid sequence. For example, an alpha-MSH monomer may comprise a single copy of a human alpha-MSH amino acid sequence as set forth in SEQ ID NO:2. Thus, in some aspects an alpha-MSH monomer of the invention may consist of the alpha-MSH sequence of SEQ ID NO:2. In some further aspects, an alpha-MSH monomer may comprise an alpha-MSH amino acid sequence with additional amino- or carboxy-terminal amino acids. In certain cases such additional amino acid sequence may encode proteolytic cleavage sites. Generally, proteolytic cleavage is the process of breaking the peptide bonds between amino acids in proteins, carried out by enzymes called peptidases, proteases or proteolytic cleavage enzymes. Proteases often recognize specific sites where the peptide bond is cleaved. For instance, in certain aspects of the invention, such cleavage sites may be positioned such that protease cleavage (e.g., cleavage in vivo following administration) results in the release of an alpha-MSH polypeptide (e.g., SEQ ID NO:2) from the remaining amino acids. Thus, in some very specific cases an alpha-MSH monomer of the invention may comprise an ACTH polypeptide.

In some aspects a an alpha-MSH monomer of the invention may comprise an ACTH polypeptide, for example an ACTH polypeptide having the sequence:

Ser$_1$ Tyr$_2$ Ser$_3$ Met$_4$ Glu$_5$ His$_6$ Phe$_7$ Arg$_8$ Trp$_9$ Gly$_{10}$ Lys$_{11}$ Pro$_{12}$

Val$_{13}$ Gly$_{14}$ Lys$_{15}$ Lys$_{16}$ Arg$_{17}$ Arg$_{18}$ Pro$_{19}$ Val$_{20}$ Lys$_{21}$ Val$_{22}$ Tyr$_{23}$ Xaa$_{24}$

Xaa$_{25}$ Xaa$_{26}$ Ala$_{27}$ Xaa$_{28}$ Xaa$_{29}$ Xaa$_{30}$ Xaa$_{31}$ Ala$_{32}$ Xaa$_{33}$ Ala$_{34}$ Phe$_{35}$ Pro$_{36}$

Xaa$_{37}$ Glu$_{38}$ Phe$_{39}$ as set forth in SEQ ID NO:13. In this instance, the amino acids (i.e., 24-26, 28-31, 33 and 37) designated by the "Xaa" notation may be any amino acid. However, in some preferred embodiments $Xaa_{24}$ may be an uncharged amino acids such as alanine or proline. In certain cases, $Xaa_{25}$ may be a charged or polar amino acid such as aspartic acid or asparagine. Preferred amino acids at the $Xaa_{26}$ position include, but are not limited to, glycine, serine and valine. Amino acid position $Xaa_{28}$ will, preferably, be a negatively charged amino acid such as aspartic acid or glutamic acid. In some further preferred embodiments $Xaa_{29}$ is an aspartic acid, glycine, glutamic acid or asparagine. Preferably, $Xaa_{30}$ and $Xaa_{33}$ will, independently, be a glutamine or glutamic acid. $Xaa_{31}$ will preferably be a serine or leucine residue. Whereas in some preferred cases, $Xaa_{37}$ is a glutamic acid or valine. In some further examples, an ACTH polypeptide for use in the current invention may be a human (SEQ ID NO:5, SEQ ID NO:6), pig (SEQ ID NO:3, SEQ ID NO:4), bovine (SEQ ID NO:7), dog (SEQ ID NO:8), elephant (SEQ ID NO:9), tamarin (SEQ ID NO:10), guinea pig (SEQ ID NO:11), rat/mouse (SEQ ID NO:12) ACTH polypeptide or a chimeric polypeptide of any of the foregoing sequences. In some preferred aspects the ACTH sequence will be a human sequence (e.g., SEQ ID NO:5 or SEQ ID NO:6) or a porcine sequence (e.g., SEQ ID NO:3) as exemplified herein.

In yet further embodiments, alpha-MSH monomers of the invention may be further defined a isolated or purified alpha-MSH monomers. For example, alpha-MSH monomers of the invention may be purified from tissues, produced recombinantly (e.g., in bacteria) or may be chemically synthesized. In preferred aspects of the invention an alpha-MSH monomer will be purified or isolated away from the bulk of other proteins in a sample. For example, in some aspects alpha-MSH may comprise at least 60%, 70%, 80%, 90%, 95%, 98%, 99% or more of the total protein in a composition or sample.

It will be understood by one of skill in the art that a peptide or polypeptide will typically comprise a free amino group at the amino terminus and a free carboxy group at the carboxy terminus. However, since these groups remain reactive in a variety of chemistries it is often preferred that the amino terminus, the carboxy terminus, or both termini of a peptide or polypeptide be blocked or protected by addition of a less reactive group. For example, the amino terminus of an alpha-MSH monomer may be blocked by an acyl group. In preferred embodiments, a peptide and/or polypeptide of the invention may comprise a dibenzyl oxy carboxyl group or an acetylated residue at the amino terminus. Thus, in some cases the $—NH_2$ terminus is replaced with $—NH—CO—CH_2$. In certain cases, a peptide or polypeptide may additionally or independently comprise an amidated (e.g., the —COOH group is replaced by $—CO—NH_2$) or esterified carboxy terminal residue. Thus, in some highly preferred aspects, a peptide or polypeptide will comprise both an amino terminal acetylated residue and a carboxy terminal amidated residue. For instance, an alpha-MSH monomer of the invention may have the amino acid sequence of SEQ ID NO:2 wherein the amino terminal residue is acetylated and the carboxy terminal residue is amidated.

The skilled artisan will readily understand that alpha-MSH monomers may be administered in a variety of forms according to the invention. For instance, an alpha-MSH monomer may be provided in liquid of solid form. In some cases, alpha-MSH monomers may be provided in a aqueous solution for direct administration or in a solution that is encapsulated in a pill or suppository. In still further aspects, an alpha-MSH monomer may be administered as an aerosol. Furthermore, in some aspects alpha-MSH monomers may be lyophilized or suspended in a gelatinous matrix. In some particular cases, an alpha-MSH monomer may be provided as a porcine ACTH polypeptide in gel matrix (e.g., a exemplified in the H.P. Acthar® Gel product). Thus, in some very specific aspects there is provided a method treating or delaying the onset of an autoimmune disease in a subject comprising enterally (e.g., orally) administering to the subject effective amount of H.P. Acthar® Gel.

In general, enteral administration means administration through the mouth (or anus). However, in some aspects, therapeutic polypeptides of the invention will be formulated such that the release of the polypeptide is delayed until the polypeptide reaches the stomach or lower gastrointestinal tract of the subject. Furthermore, in certain cases, a therapeutic polypeptide may be formulated in a tablet, capsule or suppository. Such formulations may be employed to mediate slow release of the therapeutic polypeptide over an extended period of time.

In some preferred aspects, the invention provides methods for treating or delaying the onset of an autoimmune disease in a human subject. As used herein "autoimmune disease" comprises rheumatoid arthritis, psoriasis, type 1 diabetes, systemic lupus erythematosus (SLE), transplant rejection, autoimmune thyroid disease (Hashimoto's disease), sarcoidosis, scleroderma, granulomatous vasculitis, Crohn's disease, ulcerative colitis, Sjögren's disease, ankylosing spondylitis, polymyositis dermatomyositis, polyarteritis nodosa, immunologically mediated blistering skin diseases, Behçet's syndrome, multiple sclerosis, systemic sclerosis, Goodpasture's disease or immune mediated glomerulonephritis. In some particularly preferred cases, there is provided methods for treating or delaying the onset of rheumatoid arthritis, type 1 diabetes or multiple sclerosis. In some particularly preferred aspects, a subject for treatment by methods of the invention has, or is a at risk for developing, multiple sclerosis. As used herein, a "subject" may be human or animal.

It will be understood to the skilled artisan that since some methods of the invention involve methods for delaying the onset of an autoimmune disease in some cases subjects for treatment according to the invention may be at risk for developing an autoimmune disease. For example, at risk subjects may be defined as subjects comprising autoimmune antibodies in their blood or cerebrospinal fluid. In the case MS at risk patients may be defined as having suffered precious clinical attacks or exacerbations or patients in which neuronal lesions have been detected, for example by magnetic resonance imaging (McDonald et al., 2001). In some cases, a patient at risk for developing MS is defined as a patient that presents with clinically isolated inflammatory demyelinating syndrome (CIS) and has abnormal CNS lesions as detected by magnetic resonance imaging (MRI). Such a patient may be treated according to the invention to prevent the onset of MS.

In still further embodiment of the invention there is provided a method for treating fever or inflammation in a subject comprising enterally administering to the subject an effective dose an isolated alpha-MSH monomer. For example, methods of the invention may be used to treat fever associated with bacterial or viral infections. In further aspects, a method for treating inflammation may be further defined as a method for treating atherosclerosis, asthma, psoriasis, tissue swelling, hepatic inflammation, capillary permeability, Alzheimer's disease, Parkinson's disease, muscle soreness, allergic inflammation, headache or auto-immune inflammation.

Methods of the invention may be of particular use in treating subjects with liver disease since polypeptides of the invention would not require metabolism by the liver to be cleared from the body. For example, in a specific embodiment of the invention there is provided a method for treating inflammation in a subject with impaired liver function by administering an alpha-MSH monomer of the invention or a derivative thereof. Thus, methods and compositions of the instant invention provide an alternative small molecule anti-inflammatory drugs that are metabolized in the liver. A subject with impaired liver function may in some cases be defined as comprising elevated levels of liver proteins (e.g., enzymes) in their serum. Thus, in some cases it is contemplated that subjects suffering from chronic or acute hepatitis (e.g., hepatitis A infection) may be treated by methods of the invention.

Alpha-MSH monomers of the invention may be administered according to any number of protocols. For instance, in some cases, administration will be at least once per month, once per week, once every two days, once per day, twice per day, three times per day or even more frequently. Methods of administration may involve relatively constant administration (e.g., by spiking a subjects drinking water with an alpha-MSH monomer as exemplified herein). Furthermore, in some aspects, an alpha-MSH monomer may be constantly or continuously administered to a subject having or at risk for developing an autoimmune disease. However, in other cases, an alpha-MSH monomer may be routinely administered for a time period of days, weeks, or months followed by a period of days weeks or months wherein the peptide is not administered. For example, in the case of MS a therapeutic polypeptide may be administer for a period of days weeks or months following a clinical attack (e.g., to prevent relapse).

In yet further aspects, methods of the invention may involve the administration of a second therapeutic agent before, after or concomitantly with the alpha-MSH monomer. For example the second therapeutic agent may be a soluble immune response suppressor (SIRS) polypeptide (for example, as described in U.S. patent application Ser. No. 11/570,221 which is specifically incorporated by reference herein), an interferon polypeptide (e.g., interferon alpha or tau), or an anti-inflammatory agent such as steroid. In a preferred aspect of the invention the second therapeutic agent may also be administered orally for instance as described in U.S. patent application Ser. No. 08/844,731 and PCT/US2005/002026.

In a related embodiment, there is provided an alpha-MSH monomer provided in a therapeutic, pharmaceutically acceptable formulation. In some preferred aspects for instance the alpha-MSH monomer is provided as an eye drop, nose spray, capsule, pill, tablet or suppository. An alpha-MSH monomer for use in such a formulation may be any of the alpha-MSH monomers defined herein. In some particularly preferred aspects an alpha-MSH monomer formulation is defined as formulation for enteral (e.g., oral) administration. Such a formulation may be a slow release (i.e., release over an extended time period) or delayed release formulation. Slow release pills or suppositories for instance, may be of particular use according to the invention.

In still further embodiments, therapeutic formulations of the invention may comprise an alpha-MSH monomer and a second therapeutic agent such as a SIRS polypeptide, an interferon polypeptide (e.g., interferon alpha or tau), or an anti-inflammatory agent such as steroid.

In still further embodiments, there is provided an alpha-MSH polypeptide having the amino acid sequence of SEQ ID NO:2 wherein the amino terminus is acetylated and the carboxy terminus is amidated. Such a polypeptide may have use in the methods of the of the invention. Furthermore, an alpha-MSH polypeptide having the amino acid sequence of SEQ ID NO:2 may be provided in a pharmaceutically acceptable formulation. In some preferred aspects, the alpha-MSH polypeptide is provided as an eye drop, nose spray, capsule, pill, tablet or suppository. Furthermore, as described above such a formulation may be defined as a slow release (i.e., release over an extended time period) or delayed release formulation.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Treatment of chronic autoimmune disease has proved to be a challenge even considering modern therapeutic techniques. Typical therapies involve the administration of immunosuppressive agents such as steroids. Though steroids are typically not highly effective they are well tolerated for long term use and many may be administered orally. A non-invasive method for administration, such as oral administration, is highly preferred in cases of chronic diseases such as multiple sclerosis. In some cases, immunomodulatory polypeptides have also be used for as therapeutics for autoimmune disease treatment. However, methods for administering therapeutic polypeptides typically involve intravenous or subcutaneous injection. For instance, one approved therapy utilizes an injectable porcine ACTH(H.P. ATHAR® Gel) that is administered subcutaneously. Recently, it has been recognized that some polypeptides are biologically active when administered orally. However, previously it was thought that alpha-MSH polypeptides were typically not active as oral therapeutics.

The studies described here clearly demonstrate that orally administered alpha-MSH monomers can be used as a therapeutic treatment for autoimmune disease. The EAE mouse model is a well established model system for the study of human autoimmune disease, more specifically multiple sclerosis. Studies herein show that ACTH may be orally administered to mice over an extended time period with no detectable toxicity. Furthermore, the oral ACTH administration significantly reduced clinical symptoms of autoimmune disease as compared to a placebo control in the murine EAE model system. Additional, post mortem studies of the mice also demonstrated a clear reduction in the prevalence and severity of spinal cord inflammation in the EAE mice. Given the surprising effectiveness of oral ACTH in treating disease, further studies were undertaken to determine whether alpha-MSH, a proteolytic cleavage product of ACTH could be used with similar efficacy. Interestingly, the alpha-MSH was also shown to be highly effective in reducing clinical symptoms of disease when administered in an oral monomeric formulation. Thus, these studies provide the basis for a new enteral formulations of alpha-MSH polypeptides for the treatment of autoimmune disease.

Clinical severity of disease symptoms (e.g. limb weakness, ataxia, and paraplegia) may be evaluated in various ways. In one embodiment of the invention, clinical severity is graded on a numerical scale corresponding to the number or severity of symptoms observed. In a specific embodiment of the invention, clinical symptoms in a murine model are quantified as follows: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia. In another embodiment of the invention, disease symptoms are evaluated by number of inflammatory foci per CNS segment or area. In a very specific embodiment, these evaluations of inflammatory foci are conducted by direct visual observation of the subject CNS post-mortem.

Mitogen stimulation reflects non-antigen and antigen-specific responses, thus the cytokine profiles of stimulated spleen cells or stimulated CNS lymphocytes may also be used to evaluate disease. Stimulation may be provided by NK (natural killer) and T cell stimulant ConA, or MOG peptide 35-55 (SEQ ID NO:1). Thus, in one embodiment of the invention, disease is evaluated by Th1-like cytokines (e.g. IL-2, IFN-γ, IL12p70, TNF-α, IL-1β, I-TAC, RANTES), Th2-like cytokines (e.g. IL-4, IL-10, IL-13, CD30, SDF-1, TCA-3) and certain specific cytokines referred to as chemokines (e.g. G-CSF, GM-CSF, MIP-1-α, MIP-1-γ, TECK). Cytokines, including chemokines, that may be profiled to evlaute disease include, but are not limited to: BLC, CD30L, eotaxin, eotaxin-2, FAS ligand, fractalkine, G-CSF, GM-CSF, IFN-gamma, IL-1alpha, IL-1beta, IL-2, IL-3, IL-4, IL-6, IL-9, IL-10, IL-12p40, IL-12p70, IL-13, IL-17, I-TAC, KC, Leptin, LIX, lymphotactin, MCP-1, M-CSF, MIG, MIP-1-alpha, MIP-1-gamma, RANTES, SDF-1, TCA-3, TECK, TIMP-1, TIMP-2, TNF-alpha, sTNF RI, sTNF RII.

The new methods disclosed herein address one of the greatest obstacles to treating chronic disease such autoimmune disease, that is long term tolerance of the therapeutic regimen. Such tolerance takes into account not only biological tolerance, but also psychological tolerance in patients undergoing therapy. Injectable therapeutics are far from ideal for the treatment of chronic disease. Consent injection can result in lasting damage to the tissues around the injection site and is painful and inconvenient for patients. Additionally, injection of any substance into the body increases the risk for infection by bacteria or viruses that may be present in the therapeutic formulations or on the injection apparatus itself. The instant invention enables methods for oral administration of potent immunomodulatory polypeptides. Surprisingly, these polypeptides remain highly active in an oral formulation and are effective for treating autoimmune disease. These new oral therapeutic polypeptides are particularly well adapted for prolonged administration that is often required for the treatment of chronic disease.

I. Diagnosis and Therapy for Autoimmune Diseases

Diagnosis

In the case of some systemic rheumatic diseases detection of antinuclear antibodies (ANA) may be used a method for diagnosis (Breen & Golightly, 1998). Likewise, islet cell specific immune responses may be used to diagnose type I diabetes. However, in most cases clinical criteria for autoimmune diagnosis are used. In the case of MS, diagnosis is typically made using a clinical criteria or clinical criteria in combination with paraclincal data as described in McDonald et al. (2001). For example, paraclinical data from magnetic resonance imaging (MRI) or gadalinium (Gd) assisted MRI may be used as a diagnostic tool. In this case, MS may diagnosed by detection of three out of four of: 1 Gd-enhancing or 9 T2 hyperintense lesions if no Gd-enhancing lesion; 1 or more infratentorial lesions; 1 or more juxtacortical lesions; or 3 or more periventricular lesions. It has been found in the case of MS that ~90% of MS patients initially presented with clinically isolated inflammatory demyelinating syndrome (CIS). CIS presentation in combination with paraclincal data (i.e., abnormal MRI) is a strong predictor of MS. Five years after presentation with CIS ~65% of patients with abnormal MRIs developed MS while only ~3% of patients with normal MRIs go on to develop MS. Additional paraclinical assays that may be employed in MS diagnosis include detection of altered brain wave forms (potentials) or detections of oligoclonal IgG in cerebral spinal fluid.

Therapy

Alpha-MSH monomers according to the instant invention may also be used in conjunction with other therapies that are used for the treatment of inflammation and/or autoimmune diseases. Such secondary therapies can include small molecule drugs as well as therapeutic nucleic acids or polypeptides. Anti-inflammatory agents, for example, are agents that decrease the signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the NSAIDs comprising ibuprofen include Advil, Motrin IB, Nuprin; NSAIDs comprising acetaminophens include. Tylenol; NSAIDs comprising naproxen include Aleve.

As discussed supra, certain known immunomodulatory polypeptides may also be used in accordance with the invention. Such polypeptides include, but are not limited to, SIRS, interferon-alpha and interferon-tau.

II. Therapeutic Compositions

Pharmaceutical compositions of the present invention comprise an effective amount of an alpha-MSH monomer and at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains an alpha-MSH monomer or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, gels (e.g., gelatin), dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

A pharmaceutical composition of the present invention comprising an alpha-MSH monomoer may also comprise different types of carriers depending on whether it is to be administered in solid, liquid or aerosol form, and whether it need to be sterile. The present invention can be administered intranasally, intravitreally, intravaginally, intrarectally, topically, mucosally, intraocularally, orally, topically, locally, via inhalation (e.g. aerosol inhalation), via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In the case of proteinacious compositions of the invention, it may also be preferable that the action of proteases be inhibited during storage of such alpha-MSH compositions. This can be accomplished by the additional of protease inhibitors and/or the storage of the compositions at low temperature prior to administration.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Dosages

Alpha-MSH monomers of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_5$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with alpha-MSH monomers of the invention include, but are not limited to, steroid and non-steroid anti-inflammatory agents.

Methods for estimating dose conversions between animal models and humans have previously been developed. In general these algorithms have been used to extrapolate an animal dose to a dose that would be tolerated by a human. For example, method for dose conversions have previously been disclosed by Freireich et al. (1966). The conversion methods taught by Freireich calculate equivalent doses between species using surface area ($m^2$) rather than mass (kg), a method that correlates much more closely to actual data than body mass conversions. Specifically, Freireich teaches how to use an animal 10% lethal dosage ($LD_{10}$) value to estimate the maximum tolerated doses in a human. Freireich also discussed method for converting a dose in mg/kg to a dose in mg/$m^2$ by using the "km" conversion factor for the given animal. For example, in the case of a laboratory mouse the km is approximately 3.0. Thus, in mice mg/$m^2$=$k_m$ (3.0 for mice) X dose in mg/kg.

More recent studies regarding species dose scaling have further elaborated upon the methods of Freireich. These newer studies have reduced error associated with conversion between species to determine human tolerable doses. For example, Watanabe et al. (1992) describes that a conversion of doses between species using body surface area may not be the most accurate method per se for predicting a human equivalent dosage. Nonetheless, the scaling factors set forth by Watanabe yield results that are within the margin of error of the older Freireich conversions. Currently accepted methods for determining a proper starting dose in humans expand upon the methods set forth by Freireich. For example, Mahmood et al. (2003) provides a discussion regarding the choice of a proper starting dose in humans given dose studies in animals.

II. Toxicity

Preferably, a therapeutically effective dose of alpha-MSH monomer described herein will provide therapeutic benefit without causing substantial toxicity.

Toxicity of the molecules described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975).

III. Polypeptides

In additional aspects of the invention alpha-MSH monomers (e.g, ACTH molecules) may be further modified by amino substitutions, for example by substituting an amino acid at one or more positions with an amino acid having a similar hydropathic. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in alpha-MSH and will likely only have minor effects on their activity and in vivo efficacy. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the alpha-MSH monomers described herein may be modified by the substitution of an amino acid, for different, but homologous amino acid with a similar hydrophilicity value. Amino acids with hydrophilicities within +/−1.0, or +/−0.5 points are considered homologous.

It will also be understood that certain amino acids have specific properties, and thus any amino acid substitution will abolish said property. For example cysteine residues have the unique ability to form di-sulfide bonds, that can be crucial for protein structure and activity. Thus, a substitution of cysteine residue for any other amino acid may be expected, by one of skill in the art, to alter the activity of a protein.

Furthermore, alpha-MSH monomers may comprise one or more modified or unusual amino acid such as 2 Aminoadipic acid, 3 Aminoadipic acid, β alanine, β Amino propionic acid, 2 Aminobutyric acid, 4 Aminobutyric acid, piperidinic acid, 6 Aminocaproic acid, 2 Aminoheptanoic acid, 2 Aminoisobutyric acid, 3 Aminoisobutyric acid, 2 Aminopimelic acid, alpha-methyl leucine, 2,4 Diaminobutyric acid, Desmosine, 2,2' Diaminopimelic acid, 2,3 Diaminopropionic acid, N Ethylglycine, N Ethylasparagine, Hydroxylysine, allo Hydroxylysine, 3 Hydroxyproline, 4 Hydroxyproline, Isodesmosine, allo Isoleucine, Acetylated-lysine, N Methylglycine, sarcosine, N Methylisoleucine, 6 N Methyllysine, N Methylvaline, Norvaline, Norleucine or Ornithine. For example norleucine, a non-templated amino acid that is formed by deamination of lysine, may be substituted at one or more positions. In certain cases alpha-MSH monomers of the invention may incorporate amino acids of the "D" chirality that do not naturally occur in proteins, and are thereby resistance to degradation.

In a some embodiments, alpha-MSH monomers may be from cells that are made to over express the protein. For instance cells may be transformed with a nucleic acid vector that expresses alpha-MSH polypeptide or a precursor thereof (e.g., ACTH). These cells may comprise mammalian cells, bacterial cells, yeast cell, insect cells, whole organisms, or other cells that may be a useful source recombinant protein. The alpha-MSH monomer may then be purified from the cells by method know to those of skill in the art.

In still other embodiments an alpha-MSH monomer may be purified from an animal or animal tissue. For instance, porcine ACTH may be purified from pig pituitary glands. Methods for purification of alpha-MSH monomers have been previously described for example in U.S. Pat. Nos. 2,903,471 and 2,992,165.

Thus, in certain embodiments, the invention concerns isolated DNA segments and/or recombinant vectors that encode alpha-MSH monomers. The skilled artisan will readily recognize that nucleic acids encoding an alpha-MSH monomer may be easily synthesized and cloned into an appropriate expression vector for polypeptide expression.

In some cases it may be preferable that the recombinant alpha-MSH monomers be fused with additional amino acid sequence. For example, expressed protein may be tagged for purification. Some possible fusion proteins that could be generated include histadine tags, Glutathione S-transferase (GST), Maltose binding protein (MBP), Flag and myc tagged alpha-MSH. These additional sequences may be used to aid in purification of the recombinant protein, and in some cases may then be removed by protease cleavage. For example coding sequence for a specific protease cleavage site may be inserted between the alpha-MSH coding sequence and the purification tag coding sequence. One example for such a sequence is the cleavage site for thrombin. Thus fusion proteins may be cleaved with the protease to free the alpha-MSH monomer from the purification tag. In further embodiments, recombinant an alpha-MSH monomer may be further comprise a secretion signal that allow the recombinant protein to be secreted from expressing cells. Thus in some embodiments, alpha-MSH monomers may be purified from the media of expressing cells.

Any of the wide variety of vectors known to those of skill in the art could be used to express or over express proteins according to the invention. For example, plasmids, phagmids or viral vectors may be used. In certain embodiments vectors for expression of alpha-MSH may comprise a promoter sequence. In some applications the promoter sequence may be a regulated or inducible promoter. In applications in which eukaryotic expression vectors are used the vector may further comprise a poly-adenylation signal sequence. It is well understood to these of skill in the art that these vectors may be introduced in to cells by a variety of methods including but not limited to, transfection (e.g, by liposome, calcium phosphate, electroporation, particle bombardment, etc.), transformation, and viral transduction. In some additional embodiments, the expression vectors of the invention may be stably maintained in cells. For example the expression region may be integrated into the genomic DNA of the expressing cell. Alternatively or additionally, the expression vector may further comprise drug resistance marker that allow selection of cells that express the vector by treatment of a cell population with said drug.

In certain embodiments it is also contemplated that alpha-MSH monomers f may be chemically synthesized, and purified by methods know to those in the art. For example, rapid, high fidelity methods for peptide and poly peptide synthesis for instance have been described by Miranda & Alewood (1999).

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Oral ACTH Treatment of EAE Mice

EAE is a T cell mediated inflammatory autoimmune process of the CNS that resembles in some aspects the human demyelinating disease multiple sclerosis. It thus provides a useful animal model for the evaluation of potential therapies for MS. Currently, intramuscular ACTH (adreno-cortico-trophic hormone/corticotrophin; ACTHAR® Gel) is the only FDA approved treatment for MS relapses. Orally administered ACTH is examined to determine whether it can increase clinical recovery in EAE mice compared to placebo after mice show clinical signs of neurological disease. This protocol mimics clinical practice since patients are treated with ACTHAR® Gel after they experience a clinical exacerbation of their disease, albeit clinical treatment is via intramuscular injection.

Briefly, C57BL/6 mice are actively immunized with myelin oligodendroglial (MOG) peptide 35-55 (MEVGW-YRSPFSRVVHLYRNGK, SEQ ID NO:1) in Freund's Incomplete Adjuvant and followed for evidence of disease. Clinical severity is graded daily by a blinded observer as follows: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia.

At the onset of clinical disease, mice were randomized to one of 4 treatment groups, and fed with 0.1 ml of saline (mock) or 10, 100 or 1000 microgram (194 mg/ml at 80USP/ml) of ACTHAR® Gel (porcine ACTH-Ser-Tyr-Ser-Met-Glu-His-Phe-Arg-Trp-Gly-Lys-Pro-Val-Gly-Lys-Lys-Arg-Arg-Pro-Val-Lys-Val-Tyr-Pro-Asp-Gly-Ala-Glu-Asp-Gln-Leu-Ala-Glu-Ala-Phe-Pro-Leu-Glu-Phe; SEQ ID NO:3) diluted in 0.1 ml saline daily until the end of the experiment. Following administration, clinical outcome is measured in at least two ways: by comparing the difference between group active treatment scores and placebo group scores from day 26-33 post immunization, and comparing group mean scores directly (day 17-35 post-immunization). Following sacrifice, spinal cords are removed and evaluated independently for foci of inflammation by a blinded observer. Results from two repetitions of this protocol are discussed below.

Example 1-A

Mice treated with a 10 or 1000 microgram oral dose of ACTH show significantly improved recovery from EAE attack compared to placebo (10 microgram vs placebo, $p<0.03$; 1000 microgram vs placebo, $p<0.05$) comparing the difference between group active treatment and placebo group scores. There are significantly less inflammatory foci in the 10 microgram fed group (mean group inflammatory score=$3.05\pm0.3$, $p<0.008$) and 1000 microgram fed group (mean group inflammatory score=$2.27\pm0.23$, $p<0.00002$) compared to the control mock placebo group (mean daily group score=$4.72\pm0.34$). When comparing group mean scores directly, oral doses of 10, 100, and 1000 microgram all show significantly faster recovery compared to placebo (10 microgram $1.58\pm0.03$ vs placebo, $p<0.00006$; 100 microgram $2.0\pm0.06$ vs placebo, $p<0.00008$; 1000 microgram $1.99\pm0.06$ vs placebo $2.68\pm0.06$, $p<0.00009$) (See Table 1). Thus, ingested ACTH promotes significantly faster recovery from acute EAE and decreases inflammation in spinal cord.

Example 1-B

Mice treated with a 10 or 1000 microgram oral dose of ACTH show significantly improved recovery from EAE attack compared to placebo (10 IU vs placebo, $p<0.0001$; 100 IU vs placebo, $p<0.0003$; 1000 IU vs placebo, $p<0.0007$) comparing the difference between group active treatment and group placebo scores (See Table 2). When comparing group mean scores directly, oral 10 and 1000 IU ACTH shows significantly improved recovery from EAE attack compared to placebo (10 IU vs placebo, $p<0.00001$; 100 IU vs placebo, $p<0.00006$; 1000 IU vs placebo, $p<0.00003$) comparing the difference between active treatment and placebo (See Table 3).

TABLE 1

Summary of oral ACTH Therapy Treatment*

| | Day | Control | ACTH 10 | ACTH 100 | ACTH 1000 |
|---|---|---|---|---|---|
| Clinical Score | 17 | 2 | 1.63 | 2 | 1.5 |
| | 18 | 2.25 | 1.88 | 2.13 | 2.38 |
| | 19 | 2.25 | 1.63 | 2 | 2.38 |
| | 20 | 2.38 | 1.63 | 2.38 | 2.25 |
| | 21 | 2.38 | 1.63 | 2.38 | 2 |
| | 22 | 2.63 | 1.63 | 2.5 | 2.25 |
| | 23 | 2.75 | 1.75 | 2.25 | 2.25 |
| | 24 | 2.88 | 1.63 | 2.25 | 2.13 |
| | 25 | 2.63 | 1.75 | 2.25 | 2.13 |
| | 26 | 2.63 | 1.75 | 2 | 2.13 |
| | 27 | 2.75 | 1.63 | 2 | 2.13 |
| | 28 | 2.88 | 1.38 | 2 | 2 |
| | 29 | 2.88 | 1.5 | 1.75 | 1.88 |
| | 30 | 2.75 | 1.5 | 1.63 | 1.75 |
| | 31 | 2.88 | 1.5 | 1.63 | 1.75 |
| | 32 | 3 | 1.38 | 1.63 | 1.75 |
| | 33 | 3 | 1.375 | 1.75 | 1.75 |
| | 34 | 3.13 | 1.5 | 1.75 | 1.75 |
| | 35 | 3.13 | 1.38 | 1.75 | 1.75 |
| | Mean | 2.69 | 1.58 | 2 | 1.99 |
| | St Dev | 0.06 | 0.03 | 0.06 | 0.06 |
| | P value | | 0.00006 | 0.000007 | 0.000009 |

*Values represent the mean daily scores from 8 eight animals per treatment group.

TABLE 2

Summary of oral ACTH Therapy Treatment*

|  | Day | Control | ACTH 10 IU | ACTH 100 IU | ACT 1000 IU |
|---|---|---|---|---|---|
| Clinical | 25 | 2.19 | 1.69 | 1.94 | 1.88 |
| Score | 26 | 2.5 | 1.75 | 1.94 | 2.13 |
|  | 27 | 2.31 | 1.63 | 2.06 | 2.13 |
|  | 28 | 2.31 | 1.63 | 1.75 | 2 |
|  | 29 | 2.25 | 1.88 | 1.63 | 1.63 |
|  | 30 | 2.69 | 1.63 | 1.44 | 1.63 |
|  | 31 | 2.25 | 1.44 | 1.31 | 1.44 |
|  | 32 | 2.13 | 1.38 | 1.38 | 1.44 |
|  | 33 | 2 | 1 | 1.44 | 1.44 |
|  | 40 | 1.94 | 1.25 | 1.38 | 1.13 |
|  | Mean | 2.29 | 1.55 | 1.62 | 1.75 |
|  | St Dev | 0.07 | 0.09 | 0.09 | 0.1 |
|  | P value |  | 0.0001 | 0.0003 | 0.0007 |

*Values represent the mean daily scores from 8 eight animals per treatment group.

TABLE 3

Summary of oral ACTH Therapy Treatment*

|  | Day | Control | ACTH 10 IU | ACTH 100 IU | ACTH 1000 IU |
|---|---|---|---|---|---|
| Clinical | 17 | 1.5 | 1.5 | 1.63 | 1.75 |
| Score | 18 | 2.13 | 1.75 | 1.88 | 2 |
|  | 19 | 2.5 | 1.88 | 1.88 | 2 |
|  | 20 | 2.88 | 2.13 | 2 | 2.13 |
|  | 21 | 3.13 | 2.13 | 2.13 | 2.13 |
|  | 22 | 3 | 1.88 | 2.13 | 2.25 |
|  | 23 | 2.88 | 2.13 | 2.13 | 2.38 |
|  | 24 | 3 | 2 | 2.25 | 2.38 |
|  | 25 | 2.88 | 2.13 | 2.25 | 2.38 |
|  | 26 | 2.88 | 2.13 | 2.25 | 2.25 |
|  | 27 | 2.75 | 2.13 | 2.38 | 2.38 |
|  | Mean | 2.68 | 1.98 | 2.08 | 2.18 |
|  | St Dev | 0.14 | 0.06 | 0.07 | 0.06 |
|  | P value |  | 0.00001 | 0.00006 | 0.00003 |

*Values represent the mean daily scores from 8 eight animals per treatment group.

Example 2

Oral Alpha-MSH Treatment of EAE Mice

Alpha MSH is an in vivo proteolytic cleavage product of ACTH with known immunomodulatory function. Therefore the ability of oral alpha-MSH to inhibit EAE attacks in mice is examined.

Example 2-A

Figure 1:
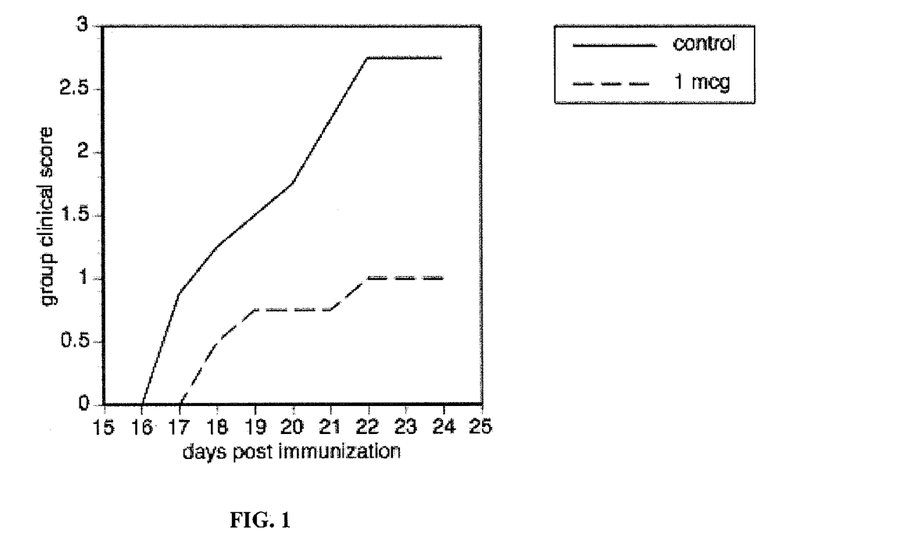
FIG. 1: One microgram ingested alpha-MSH peptide inhibits clinical EAE attacks in B6 mice. Mice (8/group) are immunized with MOG peptide 35-55 (SEQ ID NO:1) and are injected with 0.1 ml of control saline or 1 microgram alpha-MSH peptide as described in the Examples. One microgram ingested alpha-MSH peptide inhibits clinical EAE attacks ($p<0.001$, ANOVA). The figure shows combined results from 2 separate experiments (total n=16/group). Y-axis indicates clinical score and X-axis indicated days post MOG administration.

Briefly, C57BL/6 mice are actively immunized with myelin oligodendroglial (MOG) peptide 35-55 (MEVGW-YRSPFSRVVHLYRNGK, SEQ ID NO:1) in incomplete Freund's adjuvant and studies for evidence of disease. As, described above, clinical severity is graded daily. Clinical severity was graded daily as follows by a blinded observer: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate four limb weakness; 5=paraplegia with no more than moderate four limb weakness; 6=paraplegia with severe four limb weakness or severe ataxia. The mice are fed with 0.1 ml of saline (mock) or 10, 100 or 1000 microgram alpha-MSH (Ac-Ser-Tyr-Ser-Met-Glu-His-Phe-Arg-Trp-Gly-Lys-Pro-Val-NH$_2$; SEQ ID NO:2) diluted in 0.1 ml saline daily from day −7 preceding active immunization, and continuing through day +14 post immunization. Clinical outcomes are measured by comparing group mean scores directly. Following sacrifice, spinal cords are removed and evaluated independently for foci of inflammation by a blinded observer. As shown in FIG. 1 one microgram (μg) of alpha MSH peptide shows significant inhibition of EAE compared to placebo (p<0.01, ANOVA) with significant inhibition of disease severity and a prolonged delay in the onset of disease compared to placebo. In particular, administration of alpha-MSH peptide resulted in disease plateau after 22 days.

Example 2-B

Figure 2:
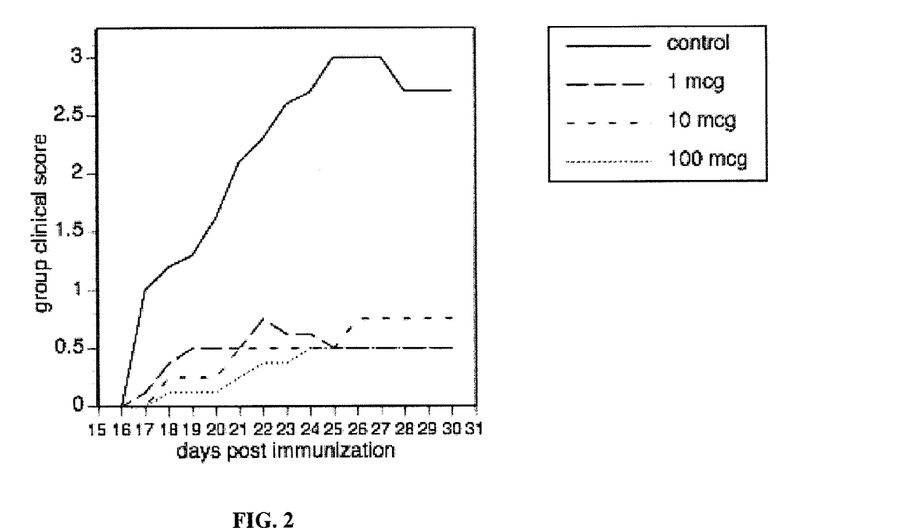
FIG. 2: 1, 10, and 100 microgram ingested alpha-MSH peptide inhibits acute EAE in B6 mice. B6 mice (n=8/group) are immunized with MOG peptide 35-55 (SEQ ID NO:1) are gavaged with 0.1 ml of control saline, 1, 10 or 100 microgram alpha-MSH peptide as described in methods. One microgram ($p<0.01$), 10 microgram g ($p<0.005$) and 100 microgram ($p<0.001$, ANOVA) alpha-MSH peptide showed a significant inhibition of disease severity compared to placebo. This experiment shows a combination of 3 separate experiments (total n=16/group). Y-axis indicates clinical score and X-axis indicated days post MOG administration.

In repeat experiments using ingested 1, 10 or 100 microgram, alpha-MSH peptide shows a significant inhibition of disease severity compared to placebo for all doses although 100 μg delayed disease onset compared to 1 microgram alpha-MSH and decreased overall disease severity compared to 10 microgram alpha-MSH (p<0.001). See FIG. 2. Ingested alpha-MSH peptide shows a dose-response effect with 100 microgram showing the most profound clinical effect.

Example 2-C

Mice are also examined histologically 30 days following immunization. There are significantly less inflammatory foci in the 1 microgram alpha-MSH peptide fed group (3.5±1.3), 10 microgram g alpha-MSH peptide fed group (5.01±1.31), 100 microgram alpha-MSH peptide fed group (2.3±0.1) compared to the control mock (saline) group (8.7±1.7) (p<0.03).

Example 2-D

The cytokine profiles of Con A stimulated spleen cells, are also compared in mock fed versus alpha-MSH peptide fed mice. Whole splenocytes (spleen lymphocytes) from mock fed mice or alpha-MSH peptide fed mice are stimulated with Con A and measured using an inflammatory cytokine antibody array. Splenocytes from 1 μg alpha-MSH peptide fed mice show increased production of BCL, CD30L, eotaxin, fractalkine, G-CSF, IL-1α, IL-9, IL-13, KC, leptin, MIP-1-α, SDF-1, TCA-3, TECK, and TNF-α (Table 4). Splenocytes from 10 μg alpha-MSH peptide fed mice show increased production of CD30L, GM-CSF, IL-1α, IL-12p70, IL-13, KC, MIP-1-α, RANTES, SDF-1, TCA-3, TECK, and TNF-α (Table 2). Splenocytes from 100 μg alpha-MSH peptide fed mice showed increased production of BCL, CD30L, GM-CSF, IL-1α, IL-2, IL-13, leptin, MIP-1-α, SDF-1, TECK, TIMP-1, and TNF-α(Table 4). There are no significant changes in Con A stimulated eotaxin-2, FAS ligand, fractalkine, IFN-γ, IL-1β, IL-3, IL-4, IL-10, IL-12p40, IL-17, lymphotactin, L1X, MCP-1/CCL2, M-CSF, MIG, MIP-1-γ and TIMP-2 between spleen cells from mock fed and alpha-MSH peptide fed mice.

Example 2-E

The cytokine profiles of Con A stimulated spleen and cord lymphocyte cells in mock fed versus 100 μg alpha-MSH peptide fed mice are also compared. Spleens and spinal cords (CNS) from each treatment group were aseptically removed and single cell suspensions prepared. In spinal cords, whole cords were passed through a cell strainer for CNS lymphocytes (B & D, Franklin Lakes, N.J.) and spun at 600 rpm several times to separate lymphocytes from CNS tissue. Splenocytes and cord lymphocytes from grouped saline fed or 100 µg alpha-MSH peptide fed mice were stimulated with the NK and T cell stimulant Con A, or with 10 µg (MOG) peptide 35-55 (MEVGWYRSPFSRVVHLYRNGK, SEQ ID NO:1). Murine cytokine responses were examined using a customized RayBio Mouse Cytokine Inflammatory Antibody Array including Th1-like (IL-2, IFN-γ, IL12p70, TNF-α, IL-1β, I-TAC, RANTES), Th2-like cytokines (IL-4, IL-10, IL-13, CD30, SDF-1, TCA-3) and chemokines important for target organ migration (G-CSF, GM-CSF, MIP-1-α, MIP-1-γ, TECK) using the RayBioantibody array Analysis tool application (RayBiotech, Inc, Norcross, Ga.). Results were grouped from mice fed saline or mice fed with 100 µg alpha-MSH peptide from grouped samples of three separate experiments (each sample performed in duplicate) and expressed as pg/ml±SEM (student t-test).

Figure 3:
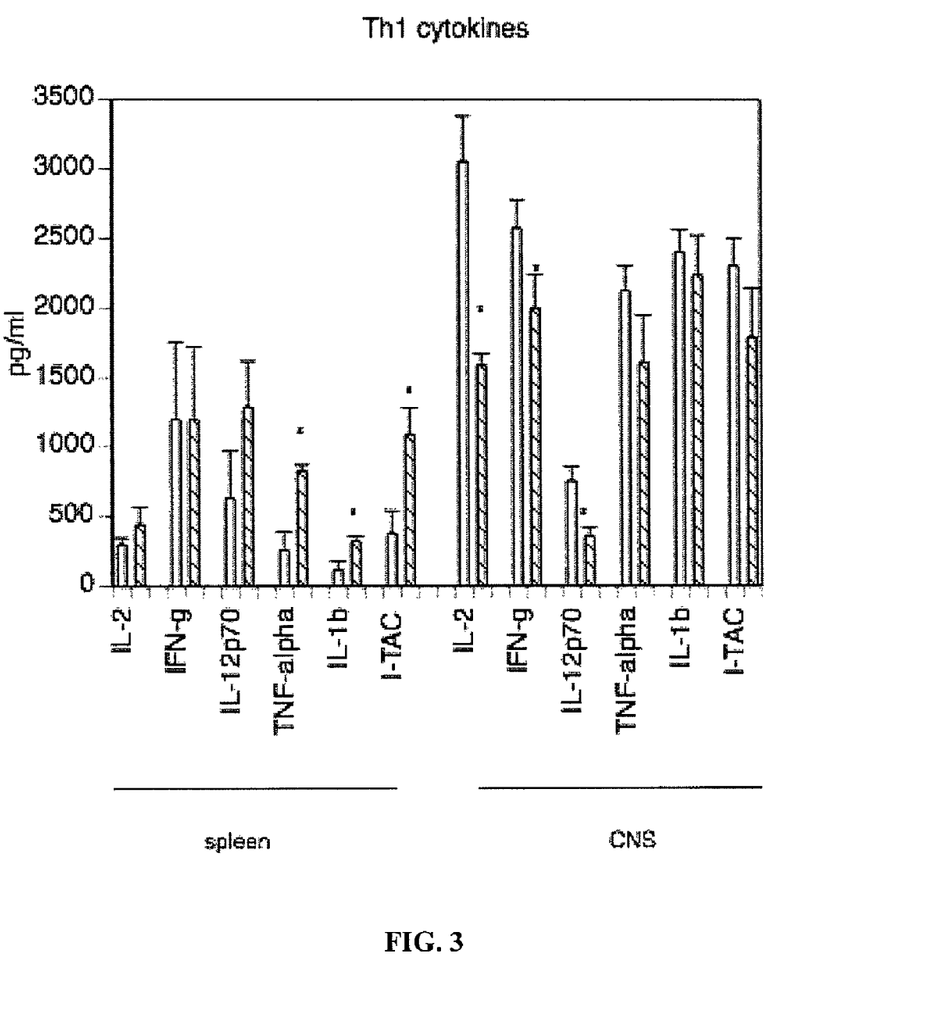
FIG. 3. Ingested alpha-MSH peptide increases splenic lymphocyte Th1-like TNF-α, IL-1β, I-TAC, but decreases CNS IL-2, IFN-γ, and IL12p70. Whole splenocytes and lymphocytes isolated from spinal cords from mock (open columns) or alpha-MSH peptide (cross hatched columns) fed mice were stimulated with Con A and evaluated in 3 separate experiments (combined; total n=16/group) using an inflammatory cytokine antibody array. Splenocytes from alpha-MSH peptide fed mice showed increased production of Th1-like TNF-α ($p<0.005$), IL-1β ($p<0.027$) and I-TAC ($p<0.04$). Lymphocytes isolated from spinal cords showed decreased Th1-like IL-2 ($p<0.05$), IFN-γ ($p<0.05$) and IL12p70 ($p<0.016$).
Figure 4:
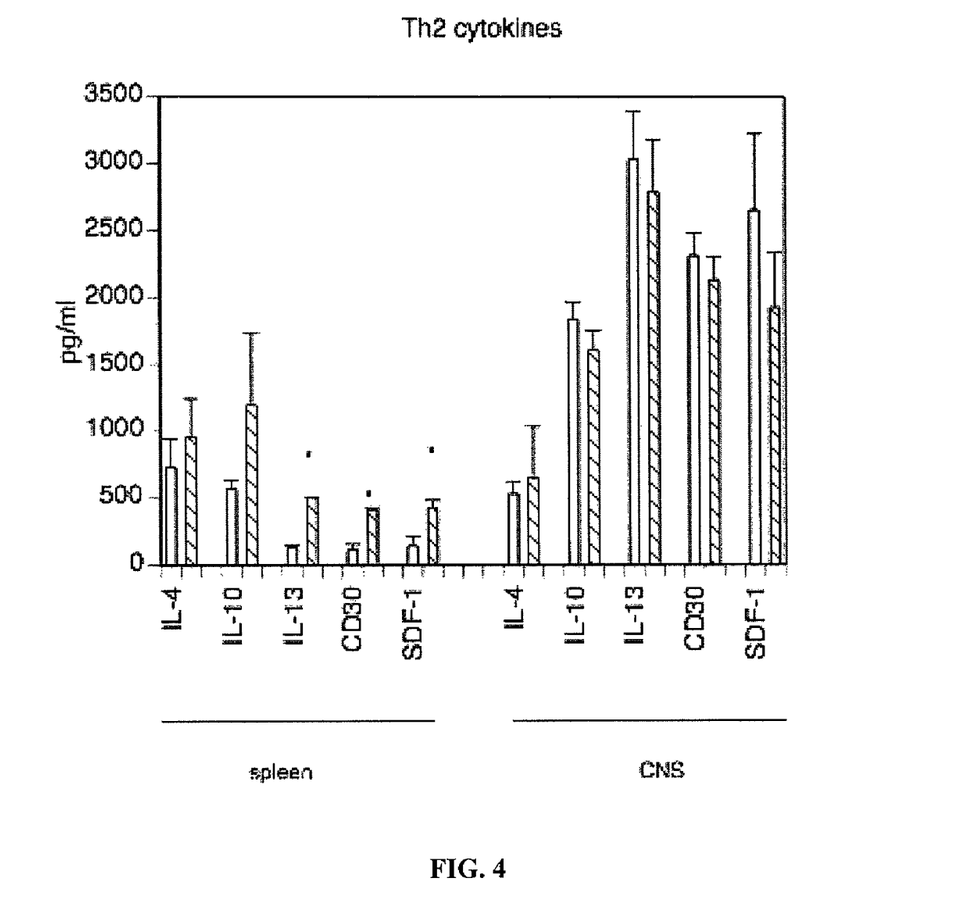
FIG. 4 Ingested alpha-MSH peptide increases in peripheral Th2-like IL-13, CD30, SDF-1 levels without increase from CNS lymphocytes. Whole splenocytes and lymphocytes isolated from spinal cords from mock (open columns) or alpha-MSH peptide (cross hatched columns) fed mice were stimulated with Con A and evaluated in 3 separate experiments (combined; total n=16/group) using an inflammatory cytokine antibody array. Splenocytes from alpha-MSH peptide fed mice showed increased production of Th2-like IL-13 ($p<0.0001$), CD30 ($p<0.0004$) and SDF-1 ($p<0.028$). Lymphocytes isolated from spinal cords from alpha-MSH peptide fed mice did not show significant changes between active and control groups.
Figure 5:
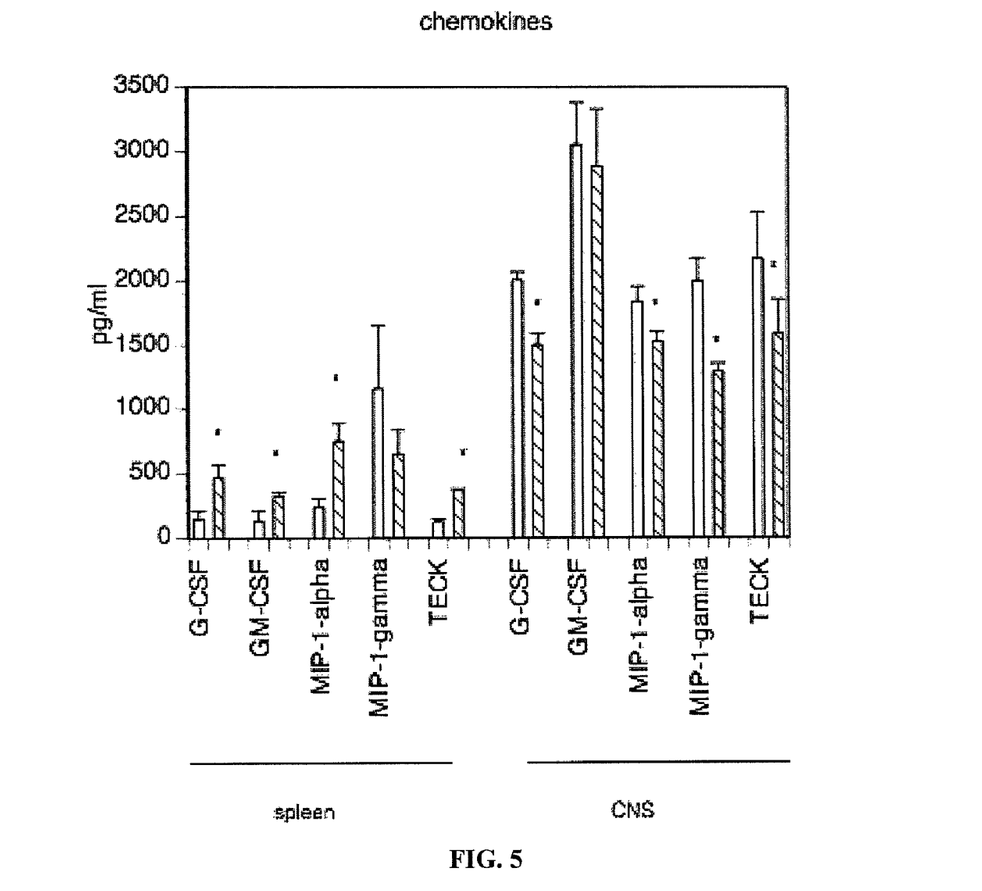
FIG. 5 Ingested alpha-MSH peptide increases splenic lymphocyte chemokine G-CSF, GM-CSF, MIP-1-α and TECK but decreases CNS G-CSF, MIP-1-α, MIP-1-γ, and TECK. Whole splenocytes and lymphocytes isolated from spinal cords from mock (open columns) or alpha-MSH peptide (cross hatched columns) fed mice were stimulated with Con A and evaluated in 3 separate experiments (combined; total n=16/group) using an inflammatory cytokine antibody array. Splenocytes from alpha-MSH peptide fed mice showed increased production of G-CSF ($p<0.05$), GM-CSF ($p<0.05$), MIP-1-α ($p<0.02$) and TECK ($p<0.0002$). Lymphocytes isolated from spinal cords from alpha-MSH peptide fed mice showed decreased G-CSF ($p<0.0001$), MIP-1-α ($p<0.05$) MIP-1-γ ($p<0.008$) and TECK ($p<0.008$).

For Th1-like cytokines, comparing alpha-MSH fed to mock fed, there was increase peripheral (splenic) lymphocyte production of TNF-α, IL-1β, I-TAC without similar increases in the CNS. See FIG. 3. In contrast, CNS lymphocytes showed decreases in levels of Th1-like cytokines IL-2, IFN-γ, and IL12p70 in the alpha-MSH fed group compared to the mock fed group. For Th2-like cytokines, there were increases in peripheral IL-13, CD30, SDF-1 levels without increase in secreted IL-13, CD30, SDF-1 from CNS lymphocytes comparing alpha-MSH fed vs mock fed groups. See FIG. 4. With regard to chemokines, there were peripheral (splenic) increases in G-CSF, GM-CSF, MIP-1-α and TECK with significant decreases of G-CSF, MIP-1-α, MIP-1-γ, TECK in the CNS comparing alpha-MSH fed mice vs mock fed mice. FIG. 5. There were no significant changes in Con A stimulated IL-4, IL-10, lymphotactin, RANTES or TCA-3 in either compartment between spleen cells and CNS lymphocytes comparing mock fed and alpha-MSH peptide fed mice.

TABLE 4

Cytokine expression following alpha-MSH administration

| Protein | Control | 1 µg | p value | 10 µg | p value | 100 µg | p value |
|---|---|---|---|---|---|---|---|
| BLC | 278 ± 68 | 983 ± 187 | 0.025 | 793 ± 281 | 0.1 | 810 ± 165 | 0.03 |
| CD30L | 168 ± 64 | 676 ± 110 | 0.017 | 633 ± 164 | 0.05 | 581 ± 101 | 0.02 |
| eotaxin | 401 ± 116 | 1037 ± 116 | 0.028 | 1066 ± 128 | 0.02 | 842 ± 90 | 0.06 |
| eotaxin-2 | 998 ± 379 | 905 ± 210 | 0.8 | 837 ± 294 | 0.25 | 750 ± 154 | 0.43 |
| FAS ligand | 78 ± 29 | 249 ± 52 | 0.04 | 204 ± 71 | 0.18 | 189 ± 65 | 0.16 |
| fractalkine | 126 ± 41 | 760 ± 104 | 0.004 | 550 ± 194 | 0.09 | 485 ± 176 | 0.09 |
| G-CSF | 215 ± 83 | 1001 ± 164 | 0.018 | 762 ± 182 | 0.08 | 785 ± 204 | 0.07 |
| GM-CSF | 142 ± 46 | 796 ± 336 | 0.09 | 1003 ± 217 | 0.006 | 615 ± 182 | 0.03 |
| IFN-gamma | 1097 ± 296 | 1467 ± 448 | 0.08 | 1467 ± 404 | 0.094 | 1160 ± 289 | 0.61 |
| IL-1alpha | 623 ± 175 | 1582 ± 176 | 0.02 | 1530 ± 161 | 0.03 | 1289 ± 123 | 0.047 |
| IL-1beta | 163 ± 62 | 627 ± 193 | 0.08 | 588 ± 251 | 0.15 | 596 ± 174 | 0.07 |
| IL-2 | 169 ± 37 | 793 ± 308 | 0.1 | 1039 ± 328 | 0.04 | 727 ± 201 | 0.044 |
| IL-3 | 743 ± 242 | 1555 ± 511 | 0.2 | 1194 ± 345 | 0.09 | 1427 ± 457 | 0.25 |
| IL-4 | 522 ± 158 | 1220 ± 239 | 0.12 | 1282 ± 288 | 0.12 | 1088 ± 196 | 0.13 |
| IL-6 | 517 ± 83 | 692 ± 318 | 0.59 | 1122 ± 452 | 0.2 | 974 ± 402 | 0.26 |
| IL-9 | 335 ± 86 | 943 ± 144 | 0.04 | 788 ± 111 | 0.06 | 645 ± 108 | 0.17 |
| IL-10 | 216 ± 68 | 1396 ± 466 | 0.07 | 938 ± 268 | 0.07 | 1009 ± 306 | 0.08 |
| IL-12p40 | 1020 ± 251 | 1687 ± 228 | 0.21 | 1747 ± 263 | 0.2 | 1928 ± 401 | 0.21 |
| IL-12p70 | 741 ± 203 | 1705 ± 270 | 0.09 | 1627 ± 188 | 0.04 | 1354 ± 174 | 0.12 |
| IL-13 | 175 ± 55 | 1072 ± 190 | 0.01 | 1038 ± 149 | 0.006 | 835 ± 205 | 0.03 |
| IL-17 | 1234 ± 462 | 1239 ± 312 | 0.98 | 789 ± 333 | 0.11 | 677 ± 145 | 0.19 |
| I-TAC | 471 ± 138 | 1077 ± 152 | 0.07 | 1053 ± 308 | 0.2 | 846 ± 178 | 0.22 |
| KC | 184 ± 61 | 512 ± 116 | 0.02 | 652 ± 172 | 0.044 | 401 ± 141 | 0.13 |
| Leptin | 444 ± 134 | 1239 ± 177 | 0.027 | 1234 ± 271 | 0.08 | 964 ± 117 | 0.04 |
| LIX | 1001 ± 402 | 1133 ± 267 | 0.45 | 1147 ± 284 | 0.67 | 996 ± 279 | 0.97 |
| lymphotactin | 1642 ± 438 | 2036 ± 454 | 0.68 | 1995 ± 246 | 0.62 | 1810 ± 438 | 0.86 |
| MCP-1 | 131 ± 288 | 720 ± 91 | 0.08 | 847 ± 297 | 0.08 | 686 ± 232 | 0.07 |
| M-CSF | 1336 ± 423 | 1855 ± 243 | 0.46 | 1910 ± 274 | 0.39 | 1468 ± 383 | 0.87 |
| MIG | 989 ± 392 | 1352 ± 410 | 0.58 | 1385 ± 447 | 0.6 | 898 ± 180 | 0.85 |
| MIP-1-alpha | 329 ± 117 | 941 ± 94 | 0.016 | 931 ± 132 | 0.047 | 872 ± 95 | 0.04 |
| MIP-1-gamma | 1740 ± 651 | 892 ± 315 | 0.36 | 1074 ± 327 | 0.43 | 1021 ± 248 | 0.38 |
| RANTES | 2089 ± 592 | 1472 ± 407 | 0.044 | 1364 ± 329 | 0.05 | 1276 ± 268 | 0.09 |
| SDF-1 | 152 ± 42 | 691 ± 96 | 0.003 | 548 ± 92 | 0.011 | 501 ± 72 | 0.002 |
| TCA-3 | 722 ± 203 | 2475 ± 450 | 0.032 | 2170 ± 381 | 0.03 | 1782 ± 308 | 0.07 |
| TECK | 164 ± 48 | 704 ± 103 | 0.01 | 537 ± 34 | 0.003 | 497 ± 83 | 0.02 |
| TIMP-1 | 571 ± 239 | 1713 ± 552 | 0.1 | 1362 ± 393 | 0.1 | 1290 ± 280 | 0.04 |
| TIMP-2 | 428 ± 136 | 1282 ± 240 | 0.06 | 1099 ± 270 | 0.14 | 1055 ± 79 | 0.02 |
| TNF-alpha | 310 ± 90 | 798 ± 150 | 0.03 | 1029 ± 157 | 0.01 | 1000 ± 113 | 0.001 |
| sTNF RI | 1314 ± 258 | 2046 ± 439 | 0.32 | 1663 ± 550 | 0.67 | 1596 ± 175 | 0.5 |
| sTNF RII | 1244 ± 343 | 1752 ± 420 | 0.52 | 1345 ± 288 | 0.87 | 1545 ± 333 | 0.65 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 2,903,471
U.S. Pat. No. 2,992,165
U.S. Pat. No. 4,554,101
U.S. Pat. No. 4,874,744
U.S. Pat. No. 5,028,592
U.S. Pat. No. 5,157,023
U.S. Pat. No. 6,338,834
U.S. Patent Appln. 20050239170
U.S. patent application Ser. No. 08/844,731
Alvord et al., *Ann NY Acad Sci.*, 122:333-345, 1965.
Breen & Golightly "Autoimmune and Rheumatic Diseases" in Saunders Manual of Clinical Laboratory Science. pp 295-384. Ed. Lehmann, W.B. Saunders Co., Philadelphia, Pa. 1998.
Brod & Bums, *Neurology*. 44:1144-1148, 1994.
Brod et al., *J Neuroimmunol*. 58:61-69, 1995.
Clackson et al., *Nature*, 352:624-628, 1991.
Feuer et al., *J Neuroimmunol.*, 10:159-166, 1985.
Fingl et al., In: *The Pharmacological Basis of Therapeutics*, 1: 1, 1975.
Freireich et al., *Cancer Chemother. Reports*, 50:219-244, 1966.
Kyte and Doolittle, *J. Mol. Biol.*, 157(1):105-132, 1982.
Mahmood et al., *J. Clin. Pharmacol.*, 43:692-697, 2003.
McDonald et al., *Annals Neurol.*, 50:121-127, 2001.
Miranda & Alewood, *Proc. Natl. Acad. Sci. USA*, 96:1181-1168, 1999.
Namba et al., *J Leukoc Biol.*, 72:946-952, 2002.
Luger et al., *Ann N Y Acad Sci.*, 994:133-140, 2003.
PCT Aplin. WO2006/021814
PCT/US2005/02026
Raine et al., *NY State J Med.*, 77:1693-1696, 1977.
Remington's Pharmaceutical Sciences, 18th Ed. Mack Printing Company, pp. 1289-1329, 1990.
Riechmann et al., *Nature*, 332:323-327, 1988.
Suresh et al., *Methods in Enzymology*, 121:210-228, 1986.
Taylor et al., *Ann N Y Acad Sci.*, 917:239-247, 2000.
Taylor et al., *Immunol Cell Biol.*, 79:358-367, 2001.
Taylor, *Cell Mol Biol (Noisy-le-grand)*, 49:143-149, 2003.
Scholzen et al., *Endocrinology*, 144:360-370, 2003.
Watanabe et al. *Risk Analysis*, 12:301-310, 1992.
Wisnewski & Keith, *Ann Neurol*. 1: 144-148, 1977.
Van der Zee et al., *Eur. J. Pharmacol.*, 147:351-357, 1988.

---

What is claimed is:

1. A method for treating or delaying the onset of multiple sclerosis in a subject comprising enterally administering to the subject an effective dose of an isolated alpha-MSH monomer, wherein the monomer consists of the amino acid sequence set forth in SEQ ID NO:2.

2. The method of claim 1, wherein the alpha-MSH monomer is administered orally.

3. The method of claim 1, wherein the subject is a human.

4. The method of claim 1, wherein the alpha-MSH monomer is blocked at the amino terminus, the carboxy terminus or both.

5. The method of claim 4, wherein the alpha-MSH monomer is acetylated at the amino terminus and amidated at the carboxy terminus.

6. The method of claim 1, wherein the alpha-MSH monomer is administered in a liquid form.

7. The method of claim 1, wherein the alpha-MSH monomer is administered in a solid form.

8. The method of claim 1, further comprising administering a second therapeutic agent before, after or concomitantly with the alpha-MSH monomer.

9. The method of claim 8, wherein the second therapeutic agent is a soluble immune response suppressor (SIRS) polypeptide, an interferon polypeptide, or an anti-inflammatory agent.

10. The method of claim 8, wherein the second therapeutic agent is administered orally.

* * * * *